| United States Patent [19] | [11] Patent Number: 4,939,249 |
| Blaszczak | [45] Date of Patent: Jul. 3, 1990 |

[54] PROCESS FOR 1-CARBA(DETHIA) CEPHALOSPORINS

[75] Inventor: Larry C. Blaszczak, Indianapolis, Ind.

[73] Assignee: Eli Lilly and Company, Indianapolis, Ind.

[21] Appl. No.: 245,185

[22] Filed: Sep. 16, 1988

[51] Int. Cl.$^5$ ............... C07D 487/04; C07D 205/085; C07B 37/06
[52] U.S. Cl. ..................................... 540/205; 540/364
[58] Field of Search ......................................... 540/205

[56] References Cited
U.S. PATENT DOCUMENTS 3,660,395  5/1972  Wright ............................. 260/243 C
3,660,396  5/1972  Wright ............................. 260/243 C

OTHER PUBLICATIONS

Kametani, T. et al., "Synthesis of Carbacepham and Carbacephem Ring Systems by Employing Radical Cyclization", *Heterocycles*, vol. 27, No. 4, 1988.
Kametani, T. et al., "Formation of Carbacephem Ring System By 1,6–Bond Coupling Through a Radical Cyclization Reaction", *Heterocycles*, vol. 19, No. 10, 1982.

*Primary Examiner*—Mark L. Berch
*Attorney, Agent, or Firm*—William B. Scanlon; Leroy Whitaker

[57] ABSTRACT

The invention provides a free radical process for preparing 1-carba(1-dethia)cephalosporin antibiotics represented by the formula

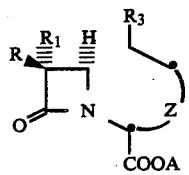

wherein R is amino or protected amino, $R_1$ is H or alkoxy, $R_3$ is H or alkyl, Z is

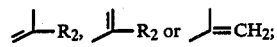

where $R_2$ is, e.g., H, halogen, or alkyl, or —$CH_2R_2'$ where $R_2'$ is, e.g., hydroxy, methoxy, or heterocyclicthio group, and A is a carboxy-protecting group which comprises heating a 2-substituted-methylcephalosporin 1,1-dioxide of the formula

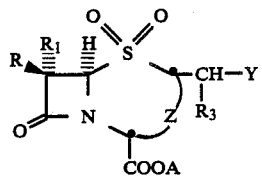

wherein R, $R_1$, $R_3$, and A are the same as in the formula above and Y is a free radical precursor group, e.g., $C_1$-$C_6$—Se—, $C_1$-$C_6$—S—, or phenyl—Se—; with a free radical initiator, e.g., a trialkyltin hydride, radiation, or a cobalt I salophen. Also provided are free radical compounds formed as intermediates in the process.

10 Claims, No Drawings

PROCESS FOR 1-CARBA(DETHIA) CEPHALOSPORINS

BACKGROUND OF THE INVENTION

This invention relates to a process for preparing 1-carba(dethia)cephalosporin antibiotic compounds. In particular, it relates to a free radical process for converting a cephalosporin 1,1-dioxide to a 1-carba(dethia)cephalosporin.

The 1-carba(dethia)cephalosporins have been obtained by total synthesis, for example, Christensen et al., U.S. Pat. No. 4,226,866, describe the preparation of 3-substituted methyl 1-carbacephalosporins, while Evans et al., U.S. Pat. No. 4,665,171, describe an asymmetric total synthesis. The 1-oxa(dethia)cephalosporins and the cephalosporins themselves have undergone extensive investigation and numerous therapeutically-useful antibiotics of these types have been developed. The 1-carba(dethia)cephalosporins have not been readily available for like investigation. Accordingly, methods for the preparation of the 1-carbacephalosporins are much sought after, particularly, methods which are amenable to large-scale production.

SUMMARY

This invention provides a process for converting a 2-substituted-methylcephalosporin 1,1-dioxide directly to a 1-carba(dethia)cephalosporin via free radical intermediates. A 2-substituted-methylcephalosporin wherein the substituent is a free radical precursor, e.g., a phenylseleno group, is heated at a temperature between about 40° C. and about 150° C. with a free radical initiator such as a trialkyltin hydride, a triaryltin hydride, a trialkyl or triarylgermane to provide the 1-carba(dethia)-3-cephem-4-carboxylic acid or ester thereof.

The 1-carba(dethia)-3-cephem product can be converted to the desired 1-carba-3-cephem antibiotic or, in certain instances, the desired antibiotic is directly obtained from the process.

DETAILED DESCRIPTION

According to the process of this invention, a 2-substituted-methylcephalosporin 1,1-dioxide represented by formula 1

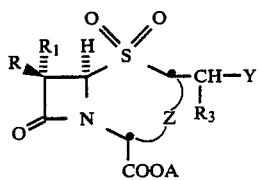

wherein
Z is a divalent group represented by the formulae

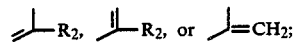

R is amino, acylamino, protected amino, or $C_1$–$C_4$ alkylsulfonylamino;
R is hydrogen or $C_1$–$C_4$ alkoxy;
Y is a free radical precursor group;
$R_2$ is hydrogen, $C_1$–$C_6$ alkyl, $C_2$–$C_6$ alkenyl, halogen, $C_1$–$C_4$ alkoxy, $C_1$–$C_4$ alkylthio, tri($C_1$–$C_4$ alkyl)silyloxy, $C_2$–$C_6$ alkanoyloxy, $C_1$–$C_4$ alkylsulfonyloxy, trifluoromethylsulfonyloxy, or a substituted methyl group represented by the formula

—$CH_2R_2'$ wherein $R_2'$ is hydroxy, $C_1$–$C_6$ alkoxy, $C_1$–$C_6$ alkanoyloxy, benzoyloxy, $C_1$–$C_6$ alkylthio, benzylthio, benzyloxy, a heterocyclicthio group wherein the heterocycle is a 5- or 6-membered heterocyclic ring containing from 1 to 4 ring nitrogen atoms and/or oxygen or sulfur ring atoms, and wherein the heterocyclic ring is bonded to the thio group via a ring carbon atom;
$R_3$ is hydrogen, or $C_1$–$C_3$ alkyl; and
A is a carboxy-protecting group;
is heated in an inert solvent at a temperature between about 45° C. and about 150° C. with a free radical initiator to form a 1-carba(dethia)cephem or cepham ester represented by formula 2

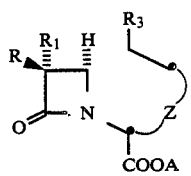

wherein R, $R_1$, $R_3$, A and Z have the same meanings as defined above.

The free radical process of this invention proceeds at a temperature between about 45° C. and about 150° C., and preferably at between about 60° C. and about 90° C. The process is best carried out in an inert solvent which can be a common organic solvent or a mixture of such solvents. For example, solvents such as ethers, alcohols, nitriles, ketones, amides and esters in which the cephalosporin sulfone 1 is at least partially soluble can be used in the process. Examples of solvents which can be used are dipropyl ether, dibutyl ether, diglyme, dioxane, ethanol, propanol, butanol, ethylene glycol, acetonitrile, butyronitrile, benzonitrile, diethyl ketone, methylisobutyl ketone, cyclohexanone, dimethylformamide, dimethylacetamide, hexamethylphosphoramide, ethyl acetate, methyl propionate, ethyl butyrate and methyl benzoate. Solvents which are known free radical scavengers or trapping agents such as nitrobenzene are to be avoided in the process.

The group Y of the cephalosporin sulfone 1 is defined herein as a "free radical precursor group". Such groups are those recognized in free radical chemistry as groups which readily provide a free radical upon interaction with free radical-generating conditions. In the context of this invention, the group Y is any group affording the free radical of formula A.

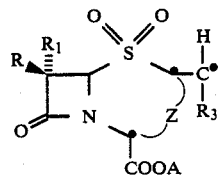

While a number of such groups are known, specific examples are selenides, $R_4Se$— or sulfides $R_4S$—, wherein $R_4$ is $C_1$–$C_6$ alkyl, $C_3$–$C_8$ cycloalkyl, $C_2$–$C_6$ alkenyl, $C_2$–$C_6$ alkinyl, phenyl, naphthyl, pyrimidinyl, tetrazolyl, pyridinyl, benzothienyl or benzofuryl; a carboxy group; a thiocarbonate, ArOC(S)O, ArS.C(S)O, wherein Ar is phenyl or naphthyl; or a heterocyclic thione ester, e.g., (N-pyridyl-2-thione)oxycarbonyl and (N-pyrimidyl-2-thione)oxycarbonyl. Y also can be a cobalt I salophen such as one formed with cobaltous ion and dibenzalethylene diamine via coordinate covalent bonding and wherein the cobalt is bonded to the 2-methylene group of 1. the free radical A is generated with the Co I salophen and radiation, e.g., UV radiation. A preferred free radical precursor group of this invention is a selenide, $R_4Se$, in particular, an aryl selenide, e.g., phenylselenide wherein Y is $C_6H_5Se-$.

Free radical initiators employed in the process can be radiation such as ultraviolet radiation produced, for example, by a mercury-vapor lamp or the like; a peroxide such as dibenzoyl peroxide, an organotin hydride such as a tri($C_1$–$C_4$ alkyl)tin hydride, a triaryltin hydride, $(Ar)_3SnH$, wherein Ar is phenyl, $C_1$–$C_4$ alkylphenyl, chlorophenyl, a triaralkyltin hydride such as tribenzyltin hydride and substituted tribenzyltin hydrides, e.g., tri-(4-methylbenzyl)tin hydride, and like organo tin hydrides; a trialkylgermane, e.g., triethylgermane, or a triarylgermane such as triphenylgermane. The preferred free radical initiators of this invention are the organo tin hydrides, in particular, trialkyl tin hydrides. Examples of these preferred tin hydrides are trimethyltin hydride, triethyltin hydride and tri-n-butyltin hydride. The organo tin hydride can be used with another free radical initiator, e.g., an azo compound such as 2-2'-azobisisobutyronitrile to enhance initiation of the process.

A peroxide initiator can initiate the free radical process with heat, while radiation will directly initiate the process.

The process of this invention proceeds rapidly and converts a cephalosporin (in the form of the sulfone) to the corresponding 1-carba(dethia)cephalosporin. The overall course of the free radical reaction involved in the process is illustrated by the following reaction scheme.

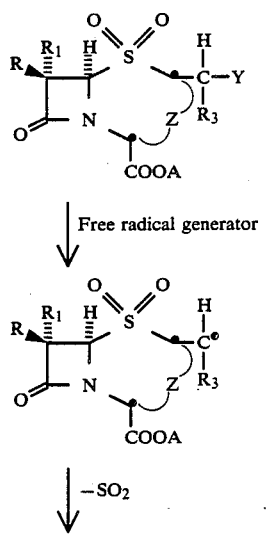

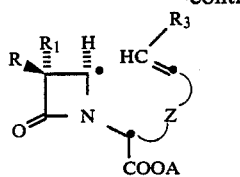
B

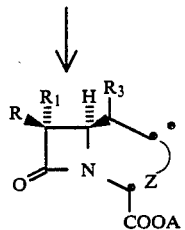
C

Termination by a hydrogen atom source

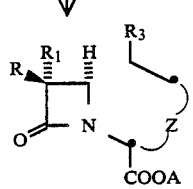
2

As is shown above, the key radical B is formed by intramolecular radical transfer of A with loss of $SO_2$. Collapse of radical B to radical C is followed by termination of the process with a hydrogen atom. The terminating hydrogen can be provided by the tin hydride employed in the process or from another source, e.g., the solvent.

The product 2 obtained in the process is recovered from the reaction mixture by conventional procedures and is separated from side products and purified by chromatography. When the starting material 1 is a 3-cephem (Z=

, the 1-carba-3-cephem product 2 is accompanied by some isomeric 1-carba-2-cephem (Z = ).

The isomer can be readily isomerized to the desired 3-cephem by treatment with a tertiary amine such as triethylamine. A side product frequently observed in the process wherein an organo tin hydride is employed is the 2,3-dimethyl-3-methyl-3-cephem sulfone ester. The latter side product is apparently formed via a 2-electron reduction rather than by a free radical course.

This invention further provides a free radical represented by the foregoing formulas A and B. These radical compounds are transient intermediates the existence of which is demonstrated not only by the product obtained via their generation as shown in the above reaction scheme but also by free radical trapping experiments. For example when the compound 1 is reacted under the process conditions described above to generate radical A, except that 10% nitrobenzene is added to the reaction mixture, the radical A is trapped and reduction products are formed via a 2-electron process instead of the described products resulting from the free radical course. The existence of these radicals also may be demonstrated by physical methods.

Preferred radical compounds of this invention are represented by formulas A and B when R is acylamino, particularly phenylacetylamino and phenoxyacetylamino; R₃ is hydrogen; and A is t-butyl, allyl or benzyl. Examples of two such preferred radicals are

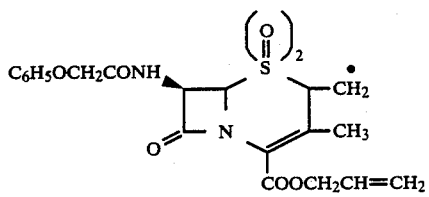

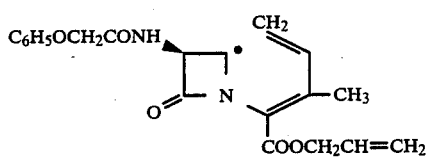

The starting material 1 can be a 7-acylamino substituted cephalosporin sulfone as defined for formula 1. Examples of such groups are those derived from carboxylic acids, in particular, the acyl groups found in the 7-position of cephalosporin and the 6-position of penicillin antibiotics. In particular, the acyl group R₄CO— of the acylamino group R₄CONH, is C₁-C₅ alkanoyl, substituted C₂-C₅ alkanoyl substituted by halogen, cyano or hydroxy; an arylacetyl or heteroarylacetyl group represented by the formula

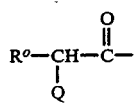

in which R° is thienyl, benzothienyl, furyl, benzofuryl, thiazolyl, oxazolyl, isoxazolyl, isothiazolyl, pyrazolyl, thiadiazolyl, oxadiazolyl, pyridyl, or these heterocyclic rings substituted by C₁-C₄ alkyl, amino, protected amino or hydroxy; cyclohexadienyl, napththyl, phenyl or a substituted phenyl group represented by the formula

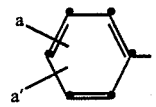

in which a and a', independently, are hydrogen, halogen, hydroxy, C₁-C₄ alkyl, C₁-C₄ alkoxy, amino, aminomethyl, methylsulfonylamino, hydroxymethyl, trifluoromethyl, carboxy, protected carboxy, carboxymethyl or protected carboxymethyl; Q is hydrogen, hydroxy, C₁-C₄ alkanoyloxy, carboxy, protected carboxy, sulfo(—SO₃H), amino, protected amino, or a substituted amino group represented by the formula

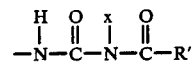

in which R' is furyl, thienyl, phenyl, halophenyl, methylphenyl, styryl, halostyryl, methylstyryl; or a group of the formula

in which R'' is hydrogen, C₁-C₄ alkyl, benzyl, C₂-C₅ alkanoyl or C₁-C₃ alkylsulfonyl; and x and y, when taken separately, are hydrogen or C₁-C₄ alkyl, and when taken together form a 5- or 6-membered ring represented by the formula

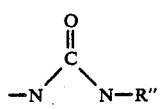

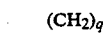

in which R'' has the same meanings as defined earlier and q is 2 or 3; or Q is a substituted amino group of the formula

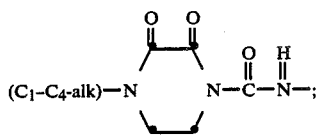

or Q is a benzamido group represented by the formula

in which b' is an integer of from 1-3; or R⁴CO is an acyl group of the formula

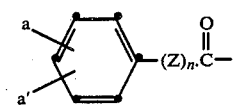

in which a and a' have the same meanings as defined earlier, Z is O or S, and n is 0 or 1; or an oximino-substituted acyl group of the formula

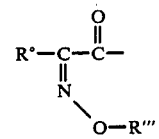

in which R° is as defined earlier, and R''' is hydrogen, C₁-C₄ alkyl, or a carboxy-substituted alkyl or cycloalkyl group of the formula

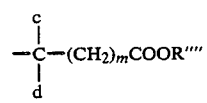

in which m is 0–3, and c and d when taken separately are, independently, hydrogen or $C_1$–$C_3$ alkyl, and when taken together with the carbon atom to which they are bonded form a 3- to 6-membered carbocyclic ring; and wherein R"" is hydrogen, $C_1$–$C_4$ alkyl, or a carboxy-protecting ester-forming group.

Examples of the acyl groups defined above when R is an acylamino group are acetyl, propionyl, cyanoacetyl, bromoacetyl, phenylacetyl, phenoxyacetyl, phenylthioacetyl, benzoyl, thienylacetyl, furylacetyl, benzothienylacetyl, benzofurylacetyl, phenylglycyl, mandeloyl, phenylmalonyl, α-sulfophenylacetyl, α-(4-hydroxybenzamido)phenylacetyl, α-(4-ethylpyrazin-2,3-dione-1-ylcarbonylamino)-α-phenylacetyl, 4-chlorophenylthioacetyl, 4-hydroxyphenylglycyl, 2,6-dimethoxybenzoyl, 3-chloro-4-hydroxyphenylglycyl, 2-(2-aminothiazol-4-yl)-2-methoxyiminoacetyl, and 2-(2-aminothiazol-4-yl)-2-carboxymethoxyiminoacetyl.

Preferred acyl groups of this invention are phenylacetyl and phenoxyacetyl.

Protected amino groups represented by R are those conventional protecting or blocking groups commonly employed for the temporary protection of an amino group. Such groups are frequently used during the preparation of a compound to prevent unwanted side reactions involving an unprotected amino group. For example, an amino group is protected or blocked when it might compete with an acylation reaction or esterification reagent directed at another site in the same molecule. Examples of such conventional protection groups are the aryl, aralkyl, alkyl, cycloalkyl or bicyclooxycarbonyl groups

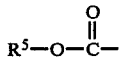

wherein $R_5$ is aryl e.g. phenyl, 4-methylphenyl, or naphthyl; aralkyl e.g. benzyl or 4-methoxybenzyl; alkyl e.g. $C_1$–$C_4$ alkyl such as methyl, ethyl or t-butyl; cycloalkyl e.g. cyclopropyl, cyclopentyl or cyclohexyl; bicycloalkyl e.g. adamantyl or bicycloheptenyl, and the like. The amino protecting group can also be an enamine such as is formed with the free amino group and a β-keto ester or β-diketone such as for example, ethyl acetoacetate, methyl acetoacetate, acetylacetone or benzoylacetone and the like. Other conventional protecting groups which can be represented by R include triphenylmethylamino, diphenylmethylamino, the "Ox" group wherein R is 4,5-diphenyl-4-oxazolin-2-one-1-yl, or the haloacetyl groups e.g. chloroacetyl or dichloroacetyl.

Carboxy protecting groups represented by A in the formula 1 are conventional protecting groups commonly used in the β-lactam art for the temporary protection or blocking of the acidic carboxy group to prevent its competition with desired reactions carried out at other sites in the molecule. Examples of such protecting groups are alkyl, alkenyl, haloalkyl, aralkyl, silyl, active esters formed with N-hydroxy compounds anhydrides, and the like. Examples of such groups are alkyl such as ethyl, t-butyl or t-amyl; alkenyl such as allyl, 2-butenyl or 2,2-dimethylpropenyl; aralkyl such as benzyl or substituted benzyl e.g. 4-methoxybenzyl or diphenylmethyl; silyl groups such as tri($C_1$–$C_4$ alkyl)silyl such as trimethylsilyl, triethylsilyl, t-butyl-dimethylsilyl or 2-(trimethylsilyl)ethyl; active esters formed with N-hydroxy compounds such as phthalimido, succinimido or benztriazole; anhydrides formed by reacting the carboxy groups with a haloformate e.g. anhydrides formed with ethyl chloroformate, methyl chloroformate or isobutyl chloroformate; anhydrides formed with other acids such as acetic acid or benzoic acid; active esters formed with phenols such as pentachlorophenol; and other conventional carboxy protecting groups such as phenacyl or chlorophenacyl.

With reference to the term $R_2$ of formula I "$C_1$–$C_6$ alkyl" refers to the straight and branched chain alkyl groups such as methyl, ethyl, n-propyl, iso-propyl, n-butyl, iso-butyl, t-butyl, n-pentyl, neopentyl, n-hexyl and the like; "$C_2$–$C_6$ alkenyl" refers to vinyl, allyl, 2-butenyl, 3-pentenyl and the like; "halogen" refers to fluoro, chloro, bromo, and iodo, "$C_1$–$C_4$ alkoxy" refers to methoxy, ethoxy, propoxy, t-butoxy, n-butoxy and the like "$C_1$–$C_4$ alkylthio"

refers to methylthio, ethylthio, propylthio, n-butylthio and the like; "tri($C_1$–$C_4$ alkyl)silyl" refers to trimethylsilyl, triethylsilyl, tri-(n-butyl)silyl, t-butyldimethylsilyl, and like groups; "$C_2$–$C_6$ alkanoyloxy" refers to acetoxy, propionoxy, butyryloxy and the like; and "$C_1$–$C_4$ alkylsulfonyloxy" refers to methylsulfonyloxy, ethylsulfonyloxy, n-butylsulfinyloxy and the like.

The term "heterocyclicthio" group represented by $R_2'$ refers to the 5- and 6-membered heterocyclic rings having a sulfur atom bonded to a ring carbon atom of the heterocycle. Examples of such groups are provided hereinafter and are named arbitrarily for convenience by naming the heterocycle and indicating the location of the bonding of the thio -S-group to the ring, e.g. pyrrol-2-thio refers to the group

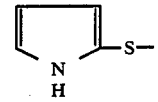

pyridin-2-thio, pyridin-3-thio, pyridin-4=thio, imidazol-2-thio, pyrazin-2-thio, pyrimidin-2-thio, s-triazin-2-thio, as-triazin-5-thio, thienyl-2-thio, furyl-2-thio, pyran-2-thio, thiopyran-2-thio; triazolyl-2-thio, oxazolyl-2-thio; 1,3,4-oxadiazolyl-2-thio, 1,3,4-thiadiazolyl-2-thio, tetrazolyl-2-thio, and like 5- and 6-membered heterocyclicthio groups.

The 2-substituted-methylsulfones represented by formula I, wherein Y is $R_4Se$— or $R_4S$—, are obtained by the reaction of a 2-methylene sulfone represented by the formula 3 below.

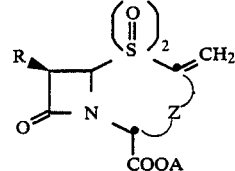

with the selenol compound $R_4SeH$ or mercaptan $R_4SH$ wherein $R_4$ has the same meanings as defined hereinabove. For example, selenophenol can be reacted with 3 to provide the 2-phenylselenomethyl sulfone 1. The reaction of the mercaptan or selenol compound can be carried out as described by Wright et al. U.S. Pat. No. 3,660,395 by substituting a cephalosporin sulfone for the cephalosporin sulfoxide employed by Wright et al. Any of the 2-thiosubstituted methyl cephalsoporin compounds described by Wright et al. can be employed in the sulfone form as starting materials in the process of the invention.

The 2-exomethylene sulfones (3) are prepared via a Mannich-type reaction of a 2-unsubstituted cephalosporin sulfone. For example, a 7-acylamino-3-methyl-3-cephem-4-carboyxlic acid ester sulfone can be reacted with the aldehyde R₃C(O)H and a secondary amine hydrochloride such as dimethylammonium chloride to provide an unstabile dimethylaminomethyl adduct. The unstabile adduct decomposes to form the 2-exomethylene cephem sulfone (3). This method for preparing (3) is described by Wright, U.S. Pat. No. 3,660,396 wherein cephalosporin in the sulfoxide form are converted to 2-exomethylene sulfoxides. Substitution of cephalosporin sulfones for the sulfoxide form used by Wright provides 3.

Examples of aldehydes R₃C(O)H are formaldehyde, acetaldehyde and propionaldehyde.

The starting material (1) wherein Y is a carboxy group can be prepared with the known 2-carboxy cephalosporin. A 2-carboxy cephalosporin ester is first oxidized to the sulfone with excess per acid e.g. m-chloroperbenzoic acid, persulfuric acid, or with permanganate. The 2-carboxy cephalsoporin sulfone is then converted to the acid chloride which on reaction with diazomethane proceeds via the Arndt-Eistert reaction to provide the 2-carboxymethyl cephalosporin sulfones (1).

Examples of cephalosporin sulfones (1) which can be used in the process of this invention are shown below in Table 1.

A preferred embodiment of the process described herein comprises the use of a compound of the formula 1 wherein Y is the group R₄Se—, R₃ is hydrogen, Z is

wherein R₂ is chloro, methyl or hydrogen, R₁ is hydrogen, R is an amino-protected phenylglycylamino group, A is allyl, benzyl, diphenylmethyl, or t-butyl, and the free radical initiator is tri(n-butyl)tin hydride.

Another preferred embodiment of the process comprises use of the compound (1) wherein R is phenoxyacetylamino or phenylacetylamino, R₁ is hydrogen, Z is

R₃ is hydrogen, Y is C₆H₅Se—, and A is allyl.

A further preferred embodiment of the process comprises the use of a compound of formula 1 wherein R is phenoxyacetylamino, phenylacetylamino or an amino-protecting group, R₁ and R₃ are hydrogen, Z is

wherein R₂ is methyl, hydrogen or chloro.

The following Examples are provided to further describe the invention and are not to be considered as limiting thereof.

TABLE 1

| | 2-Substituted-Methyl Cephalosporin Sulfones of Formula 1 | | | | | |
|---|---|---|---|---|---|---|
| | R | R₁ | R₂ | R₃ | Y | A |
| | | Z = $\overset{\|}{\diagup}$—R₂, $\overset{\|\|}{\diagup}$—R₂ | | | | |
| 1 | C₆H₅CH₂C(O)NH— | H | —CH₃ | H | C₆H₅Se— | allyl |
| 2 | C₆H₅OCH₂C(O)NH— | H | —Cl | H | C₆H₅Se— | allyl |
| 3 | C₆H₅OCH₂C(O)NH— | —OCH₃ | H | H | C₆H₅—S— | pMB[1] |
| 4 | C₆H₅OCH₂C(O)NH— | H | —CH=CH₂ | H | CH₃Se— | —CH₃ |
| 5 | C₆H₅CH(NH₂)C(O)NH— | H | —Cl | H | n-C₄H₉Se— | TCE[2] |
| 6 | 2-Thienylacetylamino | H | —SCH₃ | H | —COOH | allyl |
| 7 | t-C₄H₉OC(O)NH— | H | —OCH₃ | —CH₃ | C₆H₅—S— | pMB |
| 8 | t-C₄H₉OC(O)NH— | H | CH₂R₂' | H | C₆H₅—S— | pMB |
| 9 | CH₃C(O)NH— | H | —CH₂OC(O)CH₃ | H | C₂H₅Se— | t-C₄H₉ |
| 10 | C₆H₅OC(O)NH— | H | —CH₂OC(O)CH₃ | | Pyrimidin-2-Se | t-C₄H₉ |
| | | Z = $\diagup$=CH₂ | | | | |
| 11 | C₆H₅C(O)NH— | H | — | —CH₃ | n-C₄H₉Se— | DPM[3] |
| 12 | C₆H₅—CH₂C(O)NH— | H | — | H | C₆H₅Se— | DPM |
| 13 | 2-thienylacetylamino | H | — | H | pyridinyl-2-Se— | allyl |
| 14 | 2-aminothiazole-4-yl-2-methoxyimino-acetylamino | H | — | H | C₆H₅-3- | C₆H₅CH₂— |
| 15 | C₆H₅OCH₂C(O)NH— | H | — | H | 5-tetrazolyl-Se— | C₆H₅CH₂— |
| 16 | 2-furylacetylamino | H | — | H | C₆H₅—S— | C₆H₅CH₂— |
| 17 | t-CH₄H₉OC(O)NH— | H | — | C₂H₅ | C₆H₅—Se— | allyl |

[1]pMB = p-methoxybenzyl
[2]TCE = 2,2,2-trichloroethyl
[3]DPM = diphenylmethyl

PREPARATION 1

Preparation of allyl 7β-phenoxyacetylamino-2-exomethylene-3-methyl-3-cephem-4-carboxylate 1,1-dioxide A slurry of 42.85 g (200 mmole) of 7-aminodeacetoxycephalosporanic acid (7-ADCA) in 400 ml of dioxane and 200 ml of water was treated with 200 ml of 1N sodium hydroxide over 30 minutes. A solution of 29 ml (210 mmole) of phenoxyacetyl chloride in 130 ml of acetone and 100 ml of 2N sodium hydroxide were separately and simultaneousl added via dropwise addition at a rate such as to maintain the pH of the slurry at pH 8–9. The solution obtained was evaporated under vacuum to remove volatiles and extracted with diethyl ether to remove any neutral material.

The solution of sodium 7-phenoxyacetylamino-3-methyl-3-cephem-4-carboxylate was added to a solution of 71.3 g (210 mmole) of tetra-n-butylammonium hydroxide sulfate in 700 ml of methylene chloride and 700 ml of water which had been readjusted to pH 7.5 with 2N sodium hydroxide. The mixture was stirred for about 5 minutes and the methylene chloride layer was separated. The aqueous phase was extracted twice with methylene chloride and the extracts were combined with the organic layer. The organic layer was dried over magnesium sulfate and evaporated to a brown oil. The oil was dissolved in 250 ml of chloroform and 34.6 ml (400 mmole) of allyl bromide (previously filtered through activated alumina) were added with stirring. The mixture was stirred for about 19 hours at room temperature and when thin layer chromatography indicated some remaining starting material, 17 ml of allyl bromide were added and the mixture was heated to 50° C. with stirring for about 2 hours. The reaction mixture was evaporated on a rotary evaporator to remove chloroform and the concentrate was dissolved in 3:1, v:v of diethyl ether:methylene chloride and the solution extracted twice with pH 7 buffer, once with brine and was dried over magnesium sulfate. The solution was evaporated under vacuum to provide allyl 7-phenoxyacetylamino-3-methyl-3-cephem-4-carboxylate as a crude yellow solid.

The crude ester (ca. 200 mmole) was dissolved in 800 ml of DMF, the solution was cooled to 5° C., and a solution of 43.9 g (210 mmole) of m-chloroperbenzoic acid (85% tech.) in 250 ml of ethyl acetate was added at a rate such that the temperature was maintained below 25° C. After the addition was complete, thin layer chromatography showed mostly sulfoxide plus a trace of sulfone but no starting material. The mixture was then warmed to room temperature to provide a mixture of sulfoxide and sulfone. This mixture was combined with another preparation of the sulfone carried out as follows:

A solution of 24 g (59.3 mmole) of allyl 7-phenoxyacetylamino-3-methyl-3-cephem-4-carboxylate 1-oxide in 200 ml of DMF was treated at room temperature with 13.6 g (65 mmole) of m-chloroperbenzoic acid. The reaction mixture was poured into ethyl acetate and the solution extracted three times with 1:1 NHCl chloride:brine, once with pH 7 buffer, once with bicarbonate, and was dried and evaporated to dryness. The residue was combined with the sulfoxide-sulfone mixture obtained as described above and the sulfone crystallized from di-isopropyl ether-methylene chloride. The mother liquor was chromatographed via preparative HPLC to provide more sulfone product. The combined weight of sulfone obtained was 43.0 g.

To a solution of 43.0 g (102.2 mmole) of the sulfone, allyl 7β-phenoxyacetylamino-3-methyl-3-cephem-4-carboxylate, 1,1-dioxide, in 600 ml of dioxane were added 150 ml of 37% aqueous formaldehyde. The solution was stirred at room temperature and 12.64 g (155 mmole) of dimethylammonium chloride were added. The mixture was stirred at room temperature for about 2 hours and after removal of about half of the dioxane by evaporation under vacuum, a solid formed. The whole mixture including the solid was partitioned between ethyl acetate and 1:1, brine:1N HCl. The ethyl acetate layer was separated, dried over magnesium sulfate and evaporated to dryness on a rotary evaporator. The solid residue of product was crystallized from diisopropyl ether-methylene chloride. There were obtained 40.3 g (91%) of the desired product, allyl 7β-phenoxyacetylamino-2-exomethylene-3-methyl-3-cephem-4-carboxylate, 1,1-dioxide.

Mass Spectrum (field desorption): M+ 432.

UV Spectrum ($C_2H_5OH$) $\lambda$max 307 nm $\gamma=4092$, $\lambda$max 261 nm $\gamma=7558$.

IR Spectrum (KBr): 1772 cm$^{-1}$ ($\beta$-lactam carbonyl), 1732 cm$^{-1}$ (ester carbonyl).

NMR: (CDCl$_3$) $\delta$2.23 (s, 3H), 4.59 (s, 2H), 4.80 (d, 2H), 4.91 (d, 1H), 5.35 (d, 1H), 5.39 (d, 1H), 5.95 (m, 1H), 6.20 (d, 1H), 6.25 (d/d, 1H), 6.65 (d, 1H), 6.90–7.38 (aromatic H), 8.02 (d, 1H).

PREPARATION 2

Allyl 7β-phenoxyacetylamino-2-phenylselenomethyl-3-methyl-4-carboxylate, 1,1-dioxide To a solution of 1.30 g (3 mmole) of the 2-methylene sulfone, prepared as described by Preparation 1, in 10.5 ml of acetonitrile was added an excess of selenophenol and the solution was stirred at room temperature for about 30 minutes. The product precipitated from the reaction mixture and was filtered and dried under vacuum. There were obtained 446 mg of the title compound as colorless crystals. The filtrate was evaporated to dryness and the residue of product crystallized from methylene chloride - di-isopropyl ether to provide a second crop.

Mass Spectrum (field desorption): M+ 590.

UV ($C_2H_5OH$): $\lambda$max 239 nm $\epsilon=13481.6$.

NMR: (CDCl$_3$) $\delta$2.03 (s, 3H), 3.40 (d, 2H), 3.95 (t, 1H), 4.59 (s, 2H), 4.69–4.81 (m, 3H), 5.32 (d/d, 1H), 5.38 (d/d, 1H), 5.85–6.66 (m, 1H), 6.19 (d/d, 1H), 6.90–7.62 (aromatic H), 8.10 (d, 1H).

IR (KBr): 1766 cm$^{-1}$ ($\beta$-lactam carbonyl), 1727 cm$^{-1}$ (ester carbonyl).

EXAMPLE 1

Allyl 7β-phenoxyacetylamino-3-methyl-1-carba(dethia)-3-cephem-4-carboxylate

To a suspension of 5 g (8.5 mole) of allyl 7β-phenoxyacetylamino-2-phenylselenomethyl-3-methyl-3-cephem-4-carboxylate 1,1-dioxide and 2.62 g (16 mmole) of azobisisobutylronitrile in 100 ml of diglyme were added 6.77 ml (25.7 mmole) of tri-n-butyltin hydride. The reaction mixture was heated to a temperature of about 100° C. Gas began evolving from the reaction mixture at a temperature of about 86° C. and subsided after about 15 minutes. The maximum temperature reached 112° C.

After 25 min. a thin layer chromatogram was run on a small aliquot of the mixture using ethyl acetate:methylene chloride, 15:85, v/v. The chromatogram showed that all of the starting material had reacted.

The reaction mixture was then evaporated to remove the diglyme and the residue was dissolved in acetonitrile. The solution was washed with pentane and evaporated to dryness to yield 8.9 g of a yellow oil. The oil was chromatographed on Florisil, eluting first with methylene chloride, next with ethyl acetate:methylene chloride, 20:80, v/v, and then with ethyl acetate. Multiple fractions were collected. The early fractions provided 1.12 g of allyl 7β-phenoxyacetylamino-2-(tri-n-butyltin)methyl-3-methyl-3-cephem-4-carboxylate 1,1-dioxide. The middle fractions contained 1.66 g of unidentified reduction products, while the end fractions afforded 0.93 g of a mixture of the 1-carba-3-cephem and reduction products. The mixture showed 3 spots on thin layer chromatography on silica gel using ethyl acetate:hexane, 60:40, v:v.

The mixture of 1-carba-3-cephem and reduction products was chromatographed over silica gel using a gradient of 0 to 60% ethyl acetate in hexane to provide (A), 19 mg of the 1-carba-3-cephem; (B), 510 mg of a mixture; and (C), 73 mg of the slower spot on the thin layer.

The 1-carba-3-cephem (A) allyl 7β-phenoxyacetylamino-3-methyl-1-carba(dethia)-3-cephem-4-carboxylate had a molecular weight of 370 as determined by mass spectrum and the following spectral properties.

UV (C$_2$H$_5$OH): λ 268; γ=8,584.

NMR (CDCl$_3$): δ 1.42 (m, 1H), 1.91 (m, 1H), 2.95 (s, 3H), 2.31 (m, 2H), 3.85 (m, 1H), 4.55 (s, 2H), 4.65–4.80 (m, 4H), 5.95 (m, 1H), 6.85–7.30 (aromatic H).

The mixture (B), 510 mg, was chromatographed over silica gel via gradient elution to provide 49 mg of allyl 7β-phenoxyacetylamino-3-methyl-1-carba(dethia)-2-cephem-4-carboxylate.

Mass Spectrum: 370=M+·

NMR (CDCl$_3$): δ180 (s, 2H), 2.40 (m, 1H), 2.62 (m, 1H), 3.80 (t, 1H), 4.55 (s, 2H), 4.82 (d, 1H), 5.30 (d, 1H) 5.40 (d, 1H), 5.70 (s, 1H), 5.95 (m, 1H), 6.90–7.42 (aromatic H).

Uv (C$_2$H$_5$OH): λ268; ε=12970,
λ275; ε=2430.

The 1-carba-3-cephem (A) has the structural formula

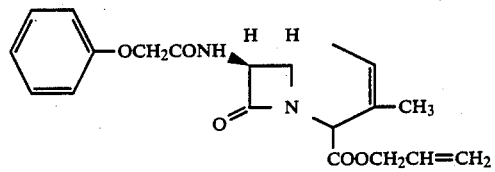

and the 1-carba-2-cephem obtained from the mixture B has the formula

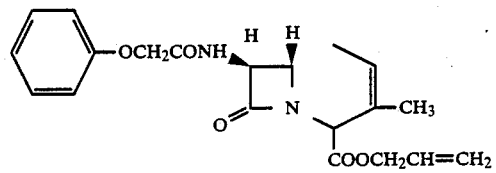

I claim:

1. A process for preparing a 1-carba(1-dethia)cephem compound of the formula

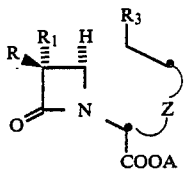

wherein
R is amino, protected amino or
R$_1$ is hydrogen or C$_1$–C$_4$ alkoxy;
Z is a divalent group of the formulae

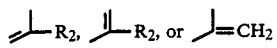

wherein R$_2$ is hydrogen, C$_1$–C$_6$ alkyl, C$_2$–C$_6$ alkenyl, halogen, C$_1$–C$_4$ alkoxy, C$_1$–C$_4$ alkylthio, tri(C$_1$–C$_4$ alkyl)silyloxy, C$_2$–C$_6$ alkanoyloxy, C$_1$–C$_4$ alkylsulfonyloxy, trifluoromethylsulfonyloxy, or a substituted methyl group of the formula

wherein R$_2$' is hydroxy, C$_1$–C$_6$ alkoxy, C$_1$–C$_6$ alkanoyloxy, benzyloxy, C$_1$–C$_6$ alkylthio, benzylthio, a hetero-cyclicthio group wherein the heterocycle is a 5- or 6-membered heterocyclic ring containing from 1 to 4 ring nitrogen atoms and/or oxygen or sulfur ring atoms and wherein the heterocyclic ring is bonded to the thio group via a ring carbon atom;
R$_3$ is hydrogen or C$_1$–C$_3$ alkyl; and
A is a carboxy-protecting group;
which comprises heating in an inert solvent at a temperature between about 45° C. and about 150° C. a 2-substituted methylcephalosporin 1,1-dioxide of the formula

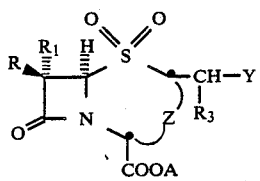

wherein R, R$_1$, R$_3$ and A have the above-defined meanings and Y is a free radical precursor group; with a free radical initiator.

2. The process of claim 1 wherein R is an amino or acylamino group, R$_1$ and R$_3$ are hydrogen, and Z is

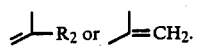

3. The process of claim 1 wherein Y is a free radical precursor group of the formula

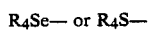

wherein R$_4$ is C$_1$–C$_4$ alkyl, C$_3$–C$_8$ cycloalkyl, C$_2$–C$_6$ alkenyl, C$_2$–C$_6$ alkinyl, phenyl, naphthyl, pyrimidinyl, tetrazolyl, pyridinyl, benzothienyl, or benzofuryl.

4. The process of claim 3 wherein the free radical initiator is a trialkyltin hydride.

5. The process of claim 4 wherein the initiator is tri-(n-butyl)tin hydride.

6. The process of claim 3 wherein R is an acylamino group $R^4CONH-$, wherein $R^4CO$ is $C_1-C_5$ alkanoyl, $C_2-C_5$ alkanoyl substituted by halogen, cyano or hydroxy; an arylacetyl or heteroarylacetyl group of the formula

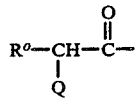

in which $R°$ is thienyl, benzothienyl, furyl, benzofuryl, thiazolyl, oxazolyl, isoxazolyl, isothiazolyl, pyrazolyl, thiadiazolyl, oxadiazolyl, pyridyl, or these heterocyclic rings substituted by $C_1-C_4$ alkyl, amino, protected amino or hydroxy; cyclohexadienyl, napththyl, phenyl or a substituted phenyl group represented by the formula

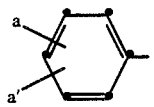

in which a and a', independently, are hydrogen, halogen, hydroxy, $C_1-C_4$ alkyl, $C_1-C_4$ alkoxy, amino, aminomethyl, methylsulfonylamino, hydroxymethyl, trifluoromethyl, carboxy, protected carboxy, carboxymethyl or protected carboxymethyl; Q is hydrogen, hydroxy, $C_1-C_4$ alkanoyloxy, carboxy, protected carboxy, sulfo, amino, or a substituted amino group represented by the formula

in which R' is furyl, thienyl, phenyl, halophenyl, methylphenyl, styryl, halostyryl, methylstyryl; or a group of the formula

in which R'' is hydrogen, $C_1-C_4$ alkyl, benzyl, $C_2-C_5$ alkanoyl or $C_1-C_3$ alkylsulfonyl; and x and y, when taken separately, are hydrogen or $C_1-C_4$ alkyl, and when taken together form a 5- or 6-membered ring represented by the formula

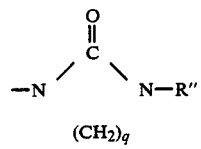

in which R'' has the same meanings as defined earlier and q is 2 or 3; or

Q is a substituted amino group of the formula

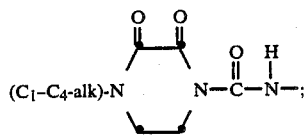

or benzamido group represented by the formula

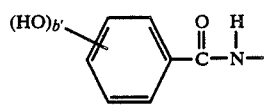

in which b' is an integer of from 1-3; or $R^4CO$ is an acyl group of the formula

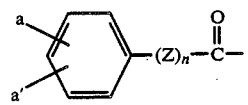

in which a and a' have the same earlier, Z is O or S, and n is 0 or 1;

or an oximino-substituted acyl group of the formula

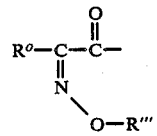

in which $R°$ is as defined earlier, and R''' is hydrogen, $C_1-C_4$ alkyl, or a carboxy-substituted alkyl or cycloalkyl group of the formula

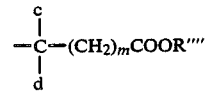

in which m is 0-3, and c and d when taken separately are, independently, hydrogen or $C_1-C_3$ alkyl, and when taken together with the carbon atom to which they are bonded form a 3- to 6-membered carbocyclic ring; and wherein R'''' is hydrogen, or a carboxy-protecting ester-forming group.

7. The process of claim 6 wherein $R_1$ and $R_3$ are hydrogen, Y is $R_4Se$ and Z is the divalent group

8. The process of claim 7 wherein the acyl group $R^4CO$ is phenoxyacetyl or phenylacetyl.

9. The process of claim 7 wherein $R^4CO$ is a phenylglycyl group.

10. The process of claim 7 wherein $R_4$ is phenyl, $R^4CO$ is phenylacetyl, $R_2$ is methyl and the free radical initiator is a trialkyltin hydride.

* * * * *

UNITED STATES PATENT AND TRADEMARK OFFICE
CERTIFICATE OF CORRECTION

PATENT NO. : 4,939,249         Page 1 of 4

DATED : July 3, 1990

INVENTOR(S) : Larry C. Blaszczak

It is certified that error appears in the above-identified patent and that said Letters Patent is hereby corrected as shown below:

Column 8, line 38, "pyridin-4=thio" should read -- pyridin-4-thio -- .

Column 10, line 68, "IN" should read -- 1N -- .

Column 12, line 13, "$\gamma$"=4092" should read -- $\varepsilon$=4092 --.

Column 12, line 14, "$\gamma$"=7558" should read -- $\varepsilon$=7558 -- .

Column 12, line 63, "v/v" should read -- v:v -- .

Column 13, line 3, "v/v" should read -- v:v -- .

Column 13, line 26, "$\gamma$=8,584" should read -- $\varepsilon$=8,584 -- .

UNITED STATES PATENT AND TRADEMARK OFFICE
CERTIFICATE OF CORRECTION

PATENT NO. : 4,939,249

DATED : July 3, 1990

INVENTOR(S) : Larry C. Blaszczak

It is certified that error appears in the above-identified patent and that said Letters Patent is hereby corrected as shown below:

Column 13, the formula between lines 45-54 reading

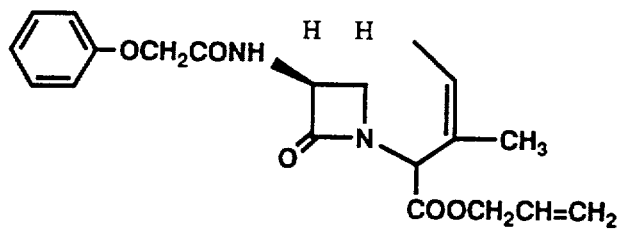

should read

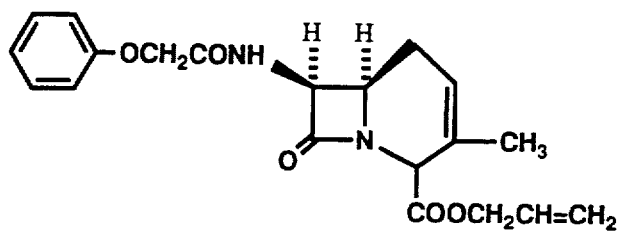

UNITED STATES PATENT AND TRADEMARK OFFICE
CERTIFICATE OF CORRECTION

PATENT NO. : 4,939,249

DATED : July 3, 1990

INVENTOR(S) : Larry C. Blaszczak

It is certified that error appears in the above-identified patent and that said Letters Patent is hereby corrected as shown below:

Column 13, the formula between lines 55-65 reading

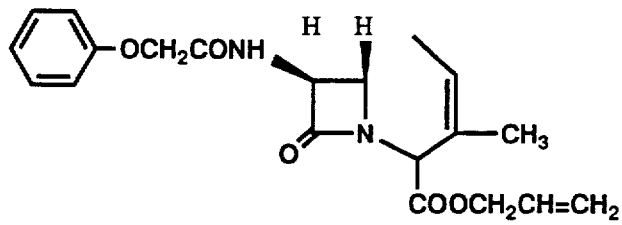

should read

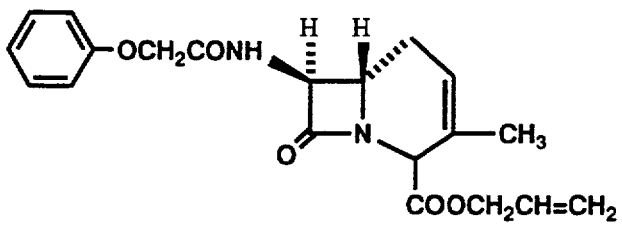

UNITED STATES PATENT AND TRADEMARK OFFICE
CERTIFICATE OF CORRECTION

PATENT NO. : 4,939,249

DATED : July 3, 1990

INVENTOR(S) : Larry C. Blaszczak

It is certified that error appears in the above-identified patent and that said Letters Patent is hereby corrected as shown below:

Column 14, line 11, "amino, protected amino or" should read -- amino, or protected amino; --.

Column 16, line 9, "or benzamido group" should read -- or Q is a benzamido group --.

Column 16, line 24, after the word "same" insert -- meanings as defined -- .

Signed and Sealed this

Thirtieth Day of November, 1993

Attest:

BRUCE LEHMAN

Attesting Officer

Commissioner of Patents and Trademarks